United States Patent
Zhou et al.

(10) Patent No.: US 10,968,489 B2
(45) Date of Patent: Apr. 6, 2021

(54) METHODS AND COMPOSITIONS FOR CHARACTERIZING DRUG RESISTANT BACTERIA FROM FORMALIN-FIXED PARAFFIN-EMBEDDED BIOLOGICAL SAMPLES

(71) Applicant: American Molecular Laboratories, Inc., Vernon Hills, IL (US)

(72) Inventors: Yi Zhou, Vernon Hills, IL (US); Daniel Jung, Vernon Hills, IL (US); Kakuturu Rao, Vernon Hills, IL (US)

(73) Assignee: AMERICAN MOLECULAR LABORATORIES INC., Vernon Hills, IL (US)

( * ) Notice: Subject to any disclaimer, the term of this patent is extended or adjusted under 35 U.S.C. 154(b) by 341 days.

(21) Appl. No.: 15/591,724

(22) Filed: May 10, 2017

(65) Prior Publication Data

US 2017/0327873 A1   Nov. 16, 2017

Related U.S. Application Data

(60) Provisional application No. 62/334,185, filed on May 10, 2016.

(51) Int. Cl.
| | | |
|---|---|---|
| *C12Q 1/689* | (2018.01) | |
| *C12Q 1/6827* | (2018.01) | |
| *C07H 21/04* | (2006.01) | |
| *G16B 30/00* | (2019.01) | |

(52) U.S. Cl.
CPC ........... *C12Q 1/689* (2013.01); *C12Q 1/6827* (2013.01); *G16B 30/00* (2019.02); *C12Q 2600/106* (2013.01); *C12Q 2600/156* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | |
|---|---|---|
| 2002/0082226 A1 | 6/2002 | Iversen |
| 2004/0052799 A1 | 3/2004 | Smith et al. |
| 2012/0108460 A1 | 5/2012 | Quake et al. |
| 2015/0307920 A1 | 10/2015 | Leamon et al. |

FOREIGN PATENT DOCUMENTS

| | | |
|---|---|---|
| CN | 104846097 A | 8/2015 |
| WO | 2015/095225 A1 | 6/2015 |

OTHER PUBLICATIONS

Schoske et al., "Multiplex PCR design strategy used for the simultaneous amplification of 10 Y chromosome short tandem repeat (STR) loci," Anal. Bioanal. Chem., vol. 375, pp. 333-343. (Year: 2003).*
Dietrich et al., "Improved PCR Performance Using Template DNA from Formalin-Fixed and Paraffin-Embedded Tissues by Overcoming PCR Inhibition," PLoS One, Oct., vol. 8, No. 10, e77771, pp. 1-10. (Year: 2013).*
Mitsui et al., "Multiplexed resequencing analysis to identify rare variants in pooled DNA with barcode indexing using next-generation sequencer," Journal of Human Genetics, May, vol. 55, pp. 448-455. (Year: 2010).*
Kaplinski et al., "MultPLX: automatic grouping and evaluation of PCR primers," Bioinformatics, vol. 21, No. 8, pp. 1701-1702. (Year: 2005).*
Ng et al., "Multiplex PCR for the detection of tetracycline resistant genes," Molecular and Cellular Probes, vol. 15, pp. 209-215. (Year: 2001).*

* cited by examiner

*Primary Examiner* — Young J Kim
(74) *Attorney, Agent, or Firm* — Morgan, Lewis & Bockius LLP; Christopher J. Betti

(57) ABSTRACT

The invention provides methods and compositions generally useful to the use of polymerase chain reaction (PCR) amplification of trace DNA sequences from formalin-fixed paraffin-embedded (FFPE) biopsy samples and specifically relevant to the identification of multi-drug resistant *H. pylori* in such biopsy samples.

16 Claims, 9 Drawing Sheets

Specification includes a Sequence Listing.

Figure 2

PCR primers.

| Pool | Amplicon | Amplicon size (bp) | PCR Primer Sequences (SEQ ID NO.) |
|---|---|---|---|
| rdxA-F1 | rdxA 188 | 188 | TGGTAATTGTTTCGTTAGGGAT (SEQ ID NO. 23)<br>TGGCGATTTCAGCGATTT (SEQ ID NO. 24) |
| | rdxA 156 | 156 | AAGCGCTTCAGCGTTAAT (SEQ ID NO. 25)<br>TGCATGCTGTGGTTGAAT (SEQ ID NO. 26) |
| | rdxA 177 | 177 | GAAGAGCGTATCAATAAGCCTAAA (SEQ ID NO. 27)<br>ATGCCACTCCTTGAACTTTAAT (SEQ ID NO. 28) |
| rdxA-F2 | rdxA -5-2-163 | 163 | AGCCTCCAATAATGCAACTATCC (SEQ ID NO. 29)<br>CATACCACCATTAACGCTGAAG (SEQ ID NO. 30) |
| | rdxA 182 | 182 | ATGCTTGGCGTGAGATTC (SEQ ID NO. 31)<br>GGCTTATTGATACGCTCTTCT (SEQ ID NO. 32) |
| rdxA-R1 | rdxA-R-150 | 150 | ATGCCACTCCTTGAACTTTA (SEQ ID NO. 33)<br>GCATGCTTGATCGCTTTG (SEQ ID NO. 34) |
| | rdxA-R-164 | 164 | ATGCAACTATCCAATCCCATTA (SEQ ID NO. 35)<br>CCGGAGTCTTATAAAGTTAGAGTG (SEQ ID NO. 36) |
| | rdxA-R-171 | 171 | GTGCGCTGCAATTTGTTT (SEQ ID NO. 37)<br>TTAAACGAGCGCCATTCTT (SEQ ID NO. 38) |
| rdxA-R2 | rdxA-R-187 | 187 | CAACCAAGTAATCGCATCAAC (SEQ ID NO. 39)<br>CATGGGCGTGAGCTTAAT (SEQ ID NO. 40) |
| | rdxA-R-174 | 174 | CTAACTTTATAAGACTCCGGATAGA (SEQ ID NO. 41)<br>TGTGATGGTTACTGATAAGGAT (SEQ ID NO. 42) |
| | rdxA-R-189 | 189 | CTGGCGATTTCAGCGATTT (SEQ ID NO. 43)<br>TGGTAATTGTTTCGTTAGGGAT (SEQ ID NO. 44) |
| 5GF | 16SrRNA 168 | 168 | TAACGCATTAAGCATCC (SEQ ID NO. 1)<br>CCAGACACTCCACTATTT (SEQ ID NO. 2) |
| | 23SrRNA 194 | 194 | CCGACCTGCATGAAT (SEQ ID NO. 3)<br>AGCCAAAGCCCTTAC (SEQ ID NO. 4) |
| | gyrA 193 | 193 | TATGCGATGCATGAATTAG (SEQ ID NO. 5)<br>CATCAATAGAGCCAAAGTT (SEQ ID NO. 6) |
| | pbpA 159 | 159 | TTGATAATGGCTATTCC (SEQ ID NO. 7)<br>GGCTCAAGGCTTCTT (SEQ ID NO. 8) |
| | rpoB 228 | 228 | GACAAGCTCACTACCATGAG (SEQ ID NO. 9)<br>CACATCCCTGGCTTCAAA (SEQ ID NO. 10) |

Figure 2 – Continued

| | | | |
|---|---|---|---|
| 5GR | 16SrRNA 162R | 162 | CTAGCGGATTCTCTCAA (SEQ ID NO. 11)<br>CAGTAATGCAGCTAACG (SEQ ID NO. 12) |
| | 23SrRNA 170R | 170 | CATCAAGGGTGGTATCT (SEQ ID NO. 13)<br>TTGTAGTGGAGGTGAAA (SEQ ID NO. 14) |
| | gyrA 139R | 139 | CGTTATCGCCATCAATAG (SEQ ID NO. 15)<br>GGTGATGTGATTGGTAAAT (SEQ ID NO. 16) |
| | gyrA 137R | 137 | CCATCAATAGAGCCAAAG (SEQ ID NO. 17)<br>ATCGTGGGTGATGTG (SEQ ID NO. 18) |
| | pbpA 140 | 140 | TTGATAATGGCTATTCC (SEQ ID NO. 19)<br>GGTTACAAGCCCTAAA (SEQ ID NO. 20) |
| | rpoB-R-167 | 167 | TGGGACAAATTCGGCCATAA (SEQ ID NO. 21)<br>TTTCATGGGCGGTCAGC (SEQ ID NO. 22) |

| | | |
|---|---|---|
| H. pylori diagnostic 23S rRNA amplicon | 125 | ACAACCCAGACTACCAAATAAG (SEQ ID NO. 45)<br>GTGAGCTGTTACGCTTTCT (SEQ ID NO. 46) |

Reference sequences.

H. pylori 16S rRNA (SEQ ID NO. 47)
GTAATCCGTAGAGATCAAGAGGAATACTCATTGCGAGGCGACCTGCTGGAACATTACTGACGCT
GATTGCGCGAAAGCGTGGGGAGCAAACAGGATTAGATACCCTGGTAGTCCACGCCCTAAACGAT
GGATGCTAGTTGTTGGAGGGCTTAGTTTTCCAGTAATGCAGCTAACGCATTAAGCATCCCGCCT
GGGGAGTACGGTCGCAAGATTAAAATCAAAGGAATAGACGGGGACCCGCACAAGCGGTGGAGCA
TGTGGTTTAATTCGAAGATACACGAAGAACCTTACCTAGGCTTGACATTGAGAGAATCCGCTAG
AAATAGTGGAGTGTCTGGCTTGCCAGACCTTGAAAACAGGTGCTGCACGGCTGTCGTCAGCTCG
TGTCGTGAGATGTTGGGTTAAGTCCCGCAACGAGCGCAACCCCTTTTCTTAGTTGCTAACAGGT
TATGCTGAGAACTCTAAGGATACTGCCTCCGTAAGGAGGAGGAAGGTGGGGA

Figure 2 - Continued

H. pylori 23S rRNA (SEQ ID NO. 48)

CAAGTGATAATAAAAGGGGGTAGAGCCCTGATTGGGCTAGGGCTGCTCGCCGCGGTACCAAA
CCCTATCAAACTTCGAATACCTTTTATCGTATCTTGGGAGTCAGGCGGTGGGTGATAAAATC
AATCGTCAAAAGGGGAACAACCCAGACTACCAAATAAGGTCCCTAAGTTCTATTCTGAGTGG
AAAAAGATGTGTGGCTACTCAAACAACCAGGAGGTTGGCTTAGAAGCAGCCATCCTTTAAAG
AAAGCGTAACAGCTCACTGGTCTAGTGGTCATGCGCTGAAAATATAACGGGGCTAAGATAGA
CACCGAATTTGTAGATTGTGTTAAACACAGTGGTAGAAGAGCGTTCATACCAGCGTTGAAGG
TATACCGGTAAGGAGTGCTGGAGCGGTATGAAGTGAGCATGCAGGAATGAGTAACGATAAGA
TATATGAGAATTGTATCCGCCGTAAATCTAAGGTTTCCTACGCGATGGTCGTCATCGTAGGG
TTAGTCGGGTCCTAAGCCGAGTCCGAAAGGGGTAGGTGATGGCAAATTGGTTAATATTCCAA
TACCGACTGTGGAGCGTGATGGGGGGACGCATAGGGTTAAGCGAGCTAGCTGATGGAAGCGC
TAGTCTAAGGGCGTAGATTGGAGGGAAGGCAAATCCACCTCTGTATTTGAAACCCAAACAGG
CTCTTTGAGTCCTTTTAGGACAAAGGGAGAATCGCTGATACCGTCGTGCCAAGAAAAGTCTC
TAAGCATATCCATAGTCGTCCGTACCGCAAACCGACACAGGTAGATGAGATGAGTATTCTAA
GGCGCGTGAAAGAACTCTGGTTAAGGAACTCTGCAAACTAGCACCGTAAGTTCGCGATAAGG
TGTGCCACAGCGATGTGGTCTCAGCAAAGAGTCCCTCCCGACTGTTTACCAAAAACACAGCA
CTTTGCCAACTCGTAAGAGGAAGTATAAGGTGTGACGCCTGCCCGGTGCTCGAAGGTTAAGA
GGATGCGTCAGTCGCAAGATGAAGCGTTGAATTGAAGCCCGAGTAAACGGCGGCCGTAACTA
TAACGGTCCTAAGGTAGCGAAATTCCTTGTCGGTTAAATACCGACCTGCATGAATGGCGTAA
CGAGATGGGAGCTGTCTCAACCAGAGATTCAGTGAAATTGTAGTGGAGGTGAAAATTCCTCC
TACCCGCGGCAAGACGGAAAGACCCCGTGGACCTTTACTACAACTTAGCACTGCTAATGGGA
ATATCATGCGCAGGATAGGTGGGAGGCTTTGAAGTAAGGGCTTTGGCTCTTATGGAGCCATC
CTTGAGATACCACCCTTGATGTTTCTGTTAGCTAACTGGCCTGTGTTATCCACAGGCAGGAC
AATGCTTGGTGGGTAGTTTGACTGGGGCGGTCGCCTCCTAAAAAGTAACGGAGGCTTGCAAA
GGTTGGCTCATTGCGGTTGGAAATCGCAAGTTGAGTGTAATGGCACAAGCCAGCCTGACTGT
AAGACATACAAG

H. pylori gyrA (SEQ ID NO. 49)
ATGCAAGATAATTCAGTCAATGAAACAAAAAATATTGTAGAAGTGGGGATTGATTCTTCTAT
TGAAGAGAGCTATTTAGCTTATTCCATGAGCGTGATCATAGGGCGCGCTTTACCGGACGCTA
GAGATGGCTTAAAGCCCGTGCATAGGCGTATTTTGTATGCGATGCATGAATTAGGCCTTACT
TCAAAAGTCGCTTACAAAAAAGCGCTAGGATCGTGGGTGATGTGATTGGTAAATACCACCC
CCATGGCGATAATGCGGTTTATGATGCGCTAGTGAGAATGGCGCAAGATTTTTCCATGCGTT
TGGAATTAGTGGATGGGCAGGGCAACTTTGGCTCTATTGATGGCGATAACGCCGCAGCGATG
CGTTACACTGAAGCCAGAATGACTAAGGCGAGTGAAGAAATTTTAAGGGATATTGATAAAGA
CACCATTGATTTTGTGCCTAATTATGACGATACCTTAAAAGAGCCAGATATTTTACCAAGCC
GTCTGCCTAACCTTTTAGTCAATGGGGCTAATGGGATCGCTGTGGGGATGGCGA H. pylori pbpA (also known as pbp1) (SEQ ID NO. 50)
AACTAACGCGTCTAATGAAGATGAAGACAACTTAAACGCTAGCATGATCGTTACAGACACGA
GCACCGGTAAGATTTTAGCTTTAGTGGGGGGGATTGATTATAAAAAAAGCGCTTTCAATCGC
GCCACGCAAGCCAAACGGCAGTTTGGGAGCGCGATAAAGCCTTTTGTGTATCAGATCGCTTT
TGATAATGGCTATTCCACGACTTCTAAAATCCCTGATACCGCGCGAAACTTTGAAAATGGCA
ATTATAGTAAAAACAGTGAACAAAACCACGCATGGCACCCCAGCAATTATTCTCGCAAGTTT
TTAGGGCTTGTAACCTTGCAAGAAGCCTTGAGCCATTCGTTAAATCTAGCCACGATCAATTT
AAGCGATCAGCTTGGCTTTGAAAAAATTTATCAATCTTTAAGCGATATGGGGTTTAAAAACC
TCCCTAAGGACTTGTCTATTGTGTTAGGGAGCTTTGCTATCTCACCCATTGATGCAGCTGAA
AAGT

Figure 2 - Continued

H. pylori rpoB (SEQ ID NO. 51)
ATGAAGATATTATCACCACCGTTAAATACCTCATGAAGATCAAAAACAATCAAGGCAAGATT
GATGACAGGGACCACTTGGGCAATCGTAGGATTAGGGCGGTAGGGGAATTGTTGGCCAATGA
ATTGCATTCAGGTTTAGTGAAAATGCAAAAGACCATTAAAGACAAGCTCACTACCATGAGCG
GGGCTTTTGATTCGCTCATGCCCCATGACTTGGTCAATTCTAAAATGATCACAAGCACCATC
ATGGAATTTTTCATGGGCGGTCAGCTCTCGCAATTTATGGATCAAACGAATCCCTTGAGTGA
GGTTACGCACAAGCGCCGCCTTTCAGCGCTCGGCGAAGGGGGGTTGGTGAAAGACAGAGTGG
GGTTTGAAGCCAGGGATGTGCACCCCACGCATTATGGCCGAATTTGTCCCATTGAGACCCCA
GAAGGTCAAAATATCGGTCTGATCAACACCCTTTCCACTTTCACAAGAGTGAATGATTTAGG
CTTTATTGAAGCCCCTTATAAAAAGGTTGTGGATGGCAAGGTCGTGGGTGAGACGATTTATT
TGACCGCTATTCAAGAAGACAGCCACATCATCGCTCCCGCAA H. pylori rdxA (SEQ ID NO. 52)
ATTTGAGCATGGGGCAGATTTTAAGCTTATTTATGGTAATTGTTTCGTTAGGGATTTTATTG
TATGCTACAAAAAATTCTAAAAAAATAAAGGAAAATCAATGAAATTTTTGGATCAAGAAAAA
AGAAGACAATTATTAAACGAGCGCCATTCTTGCAAGATGTTTGATAGCCATTATGAGTTTTC
TAGCACAGAATTAGAAGAAATCGCTGAAATCGCCAGGCTATCGCCAAGCTCTTACAACACGC
AGCCATGGCATTTTGTGATGGTTACTGATAAGGATTTAAAAAAACAAATTGCAGCGCACAGC
TATTTCAATGAAGAGATGATTAAAAGCGCTTCAGCGTTAATGGTGGTATGCTCTTTAAGACC
CAGCGAGTTGTTACCACACGGCCACTACATGCAAAATCTCTATCCGGAGTCTTATAAAGTTA
GAGTGATCCCCTCTTTTGCTCAAATGCTTGGCGTGAGATTCAACCACAGCATGCAAAGATTA
GAAAGCTATATTTTAGAGCAATGCTATATCGCTGTGGGCAAATTTGCATGGGCGTGAGCTT
AATGGGATTGGATAGTTGCATTATTGGAGGCTTTGATCCTTTAAAGGTGGGCGAAGTTTTAG
AAGAGCGTATCAATAAGCCTAAAATCGCATGCTTGATCGCTTTGGGCAAAGGGTGGCAGAAG
CGAGTCAAAAATCAAGAAAATCAAAAGTTGATGCGATTACTTGGTTGTGATTAAACAAAATC
AAAAACTTTTTAACTATAATCAAACCTAAATTAAAGTTCAAGGAGTGGCATTTTGTTTAAAA
GAATGGTTTTAATCGCTCTTTTAGGGGTGTTTTCAAGCGTTTCATTAAGCGCTAAGAGTCTT
TTAAGAGATGATGGGATTTTAGTCTCTGATTTAAAGGGCATGAAATCAGAACTATCTGATGC
TCCTGCTTGGGTTTTTGAAGACGCTAAAGCCCCCTACGAAGAAATGGGCGTGGCGTATATCC
CTGTTAATAATAAATATTTAGGGATTGAGCAAGCGACCTT

Figure 5

| Sample ID | | 16s rRNA-Tetracycline (Wild Type: AGA) | | 23s rRNA-Clarithromycin Wild Type AA | | gyrA-Fluoroquinolones* Wild type Amino Acids: NADA | | pbs-1a-Amoxcillin Wild Type: AGA | | rpoB-Rifampins Wild Type: No amino acid change in Codon 524-545 | | rdxA_Metronidazole** Wild type: No truncation | |
|---|---|---|---|---|---|---|---|---|---|---|---|---|---|
| | | NGS | Sanger Sequencing | NGS | Sanger Sequencing | NGS | Sanger Sequencing | NGS | Sanger Sequencing | NGS | Sanger Sequencing | NGS | Sanger Sequencing |
| 1 | FFPE_B | Wt | | Wt | | ACC (p.N>T) | ACC (p.N>T) | Wt | | Wild Type | | Wild Type | |
| 2 | FFPE_BB | Wt | | Wt | | ACC (p.N>T) | ACC (p.N>T) | Wt | | Wild Type | | Wild Type | |
| 3 | FFPE_C | Wt | | Wt | Wt | CCG(p.A>P), AAT(p.D>N) | CCG(p.A>P), AAT(p.D>N) | Wt | Wt | Wild Type | Wild Type | Wild Type | |
| 4 | FFPE_D | Wt | Wt | Wt | | Wild Type | Wild Type | Wt | Wt | Wild Type | Wild Type | Wild Type | |
| 5 | FFPE_E | Wt | | Wt | | ACC (p.N>T) | ACC (p.N>T) | Wt | | Wild Type | | Wild Type | |
| 6 | FFPE_F | Wt | | Wt | | Wild Type | Wild Type | Wt | | Wild Type | | Wild Type | |
| 7 | FFPE_H | Wt | | Wt | | ACC (p.N>T) | ACC (p.N>T) | Wt | | Wild Type | | Wild Type | |
| 8 | FFPE_I | Wt | | Wt | | Wild Type | | Wt | | Wild Type | | Wild Type | |
| 9 | FFPE_J | Wt | | Wt | | AA/CC(p.N>N/T), G/AAT(p.D>D/N) | AA/CC(p.N>N/T), G/AAT(p.D>D/N) | Wt | | Wild Type | | INS AG | INS AG |
| 10 | FFPE_K | Wt | | Wt | Wt | GTG(p. D>V) | GTG(p. D>V) | Wt | | Wild Type | | Wild Type | |
| 11 | FFPE_L | Wt | | AG | AG | Wild Type | Wild Type | Wt | | Wild Type | | Wild Type | |
| 12 | FFPE_O | Wt | Wt | GA | GA | Wild Type | Wild Type | Wt | | Wild Type | | Wild Type | |
| 13 | FFPE_Q | Wt | Wt | AG | AG | ATT(p.N>I) | ATT(p.N>I) | Wt | Wt | Wild Type | Wild Type | INS G | INS G |
| 14 | FFPE_R | Wt | Wt | Wt | Wt | Wild Type | Wild Type | Wt | | Wild Type | Wild Type | DEL 11bp | DEL 11bp |
| 15 | FFPE_S | Wt | | Wt | | GGT(p.D>G) | GGT(p.D>G) | Wt | | Wild Type | | Wild Type | |
| 16 | FFPE_T | Wt | | Wt | | AAT(p. D>N) | AAT(p. D>N) | Wt | | Wild Type | | Wild Type | |

Wt: Wild Type

\* mutations in nucleotide codon sequence are shown in red with corresponding protein change in amino acid in parenthesis.
Amino acid codes: N- Asparagine, A: Alanine, D: Aspartatic Acid, T: Tyrosine, P: Proline, I: Isoleucine, V: Valine, G:Glycine
\*\* insertions or deletions in rdxA listed result in truncated protein resulting in Metronidazole resistance.

Figure 6

| NO | Sample ID | Antibiotic Gene Mutation | Mutation Frequency |
|---|---|---|---|
| 1 | B | 23S rRNA (A2143G) | 31.6% |
|   |   | gyrA (Asp91Asn) | 5.9% |
| 2 | BB | gyrA (Asp91Asn) | 9.4% |
| 3 | C | 23S rRNA (A2143G) | 34.8% |
|   |   | gyrA (Asp91Asn) | 97% |
| 4 | D | gyrA (Asp91Asn) | 35% |
| 5 | E | No mutation detected | |
| 6 | F | No mutation detected | |
| 7 | G | rdxA (Glu75*) | 16.8% |
|   |   | rdxA (Gln6*) | 18.6% |
| 8 | H | No mutation detected | |
| 9 | I | No mutation detected | |
| 10 | J | gyrA (Asp91Asn) | 44.8% |
|   |   | rdxA (Gln6*) | 7.6% |
| 11 | K | 23S rRNA (A2143G) | 42% |
| 12 | L | 23S rRNA (A2143G) | 87.8% |
| 13 | M | No mutation detected | |
| 14 | O | 23S rRNA (A2143G) | 87% |
| 15 | P | gyrA (Asp91Asn) | 5.6% |
| 16 | Q | 23S rRNA (A2143G) | 90% |
| 17 | R | No mutation detected | |
| 18 | S | gyrA (Asp91Gly) | 96.3% |
| 19 | T | gyrA (Asn87Lys) | 99.4% |
|   |   | gyrA (Asp91Asn) | 66.8% |
| 20 | U | rdxA (Glu75*) | 6.4% |
| 21 | V | No mutation detected | |
| 22 | W | No mutation detected | |
| 23 | X | No mutation detected | |
| 24 | Z | No mutation detected | |

METHODS AND COMPOSITIONS FOR CHARACTERIZING DRUG RESISTANT BACTERIA FROM FORMALIN-FIXED PARAFFIN-EMBEDDED BIOLOGICAL SAMPLES

CROSS REFERENCE TO RELATED APPLICATIONS

The present application claim priority to U.S. Provisional Patent Application Ser. No. 62/334,185, filed May 10, 2016, which is incorporated herein by reference in its entirety.

SEQUENCE LISTING

The instant application contains a Sequence Listing which has been submitted electronically in .txt format and is hereby incorporated by reference in its entirety. Said .txt copy, created on Nov. 22, 2019, is named 116110_DB1_AM Labs 5001 Sequence Listing_ST25.txt and is 20,480 bytes in size.

FIELD OF THE INVENTION

The described methods and compositions are generally relevant to the use of polymerase chain reaction (PCR) amplification of trace DNA sequences from formalin-fixed paraffin-embedded (FFPE) biopsy samples. In particular, the methods and materials facilitate PCR amplification of trace bacterial DNA sequences within human biopsy FFPE preserved samples. More particularly, the methods and compositions are suited to characterizing multi-drug resistant *Helicobacter pylori* (*H. pylori*) present in human gastric biopsy FFPE samples.

BACKGROUND OF THE INVENTION

*H. pylori* is a significant human pathogen primarily found in the stomach. *H. pylori* plays an important role in gastritis, peptic ulcers and gastric cancer. Drug resistant and multi-drug resistant strains of *H. pylori* are increasingly common and front line therapy for treating *H. pylori* usually involves triple antibiotic therapy, comprising administering a proton-pump inhibitor (PPI) and two more antibiotics, typically clarithromycin and either metronidazole or amoxicillin, simultaneously. However, such therapy is only effective if the clinical isolate against which it is targeted is not clarithromycin resistant or resistant to metronidazole or penicillin-like drugs such as amoxicillin. Other antibiotics may be used, but in each case it is critical to know whether the *H. pylori* strain afflicting the patient is predisposed to resistance to any particular antibiotic to provide effective therapeutic treatment. A number of diagnostic methods for detecting the presence of *H. pylori* have been developed including, a urea breathe test, rapid urease tests, and anti-*H. pylori* antibody tests for serum and stool samples as well as an extensive range of immunohistologic staining methods. For the most part such methods require use of cultured isolates or recently obtained clinical samples. Culture of *H. pylori* and antibiotic susceptibility testing are not commonly performed in routine practice due to the specific requirements of *H. pylori* in terms of growth and transport. It is difficult and not always successful. Furthermore, there are no good methods that allow the drug resistance profile of any *H. pylori* detected to be determined. A robust and inexpensive method capable of detecting *H. pylori* while simultaneously determining the drug resistance profile of the detected bacteria represents a significant improvement over existing technologies.

Historically, biopsy tissue, specifically gastric biopsy tissue is preserved in formalin-fixed paraffin-embedded sample (FFPE) "blocks". Such blocks do not require special handling or storage and represent a common way of preserving human biopsy materials in clinical histology laboratories. FFPE preserves the ultrastructural relationships of the embedded tissue over long periods of time, the samples are not subject to exogenous contamination and FFPE facilitates processing for histological staining and is amenable to many antibody based analyses. Unfortunately, formalin fixation, which allows immobilization of cellular matter (primarily by cross-linking nitrogenous groups in macromolecules), reduces the efficacy of many nucleic acid methods such as polymerase chain reaction (PCR) amplification of specific gene sequences in FFPE biopsy samples. The DNA-dependent DNA polymerases used for PCR amplification can neither traverse nor accurately replicate DNA sequences that are chemically cross-linked or contain many modified nitrogenous bases.

Fortunately, the level of cross-linking in most FFPE samples does not completely preclude nucleic acid analysis. The methods and compositions described here improve the efficacy of PCR amplification of such cross-linked and otherwise damaged trace DNA from biopsy FFPE samples over existing methods. Typically, PCR amplification of DNA from FFPE preserved samples is targeted to analysis of the human DNA sequences present in the biopsy and there is a relatively large amount of target DNA that can be amplified. This is important, since chemical cross-linking by formalin occurs randomly and with sufficiently high copy numbers of any given target DNA sequence within a PCR amplification reaction, it is likely that at least one or some combination of the multiple copies of the desired target DNA sequence is available for amplification and thus amenable to PCR-based analyses. Commercial kits are available for direct analysis of human DNA recovered from FFPE biopsy samples, for example Illumina's TruSeq Custom Amplicon Low Input Kit (Illumina). However, the situation is very different when applied to less abundant DNA sequences such as those of bacterial pathogens present at low copy number within the FFPE preserved tissue. In cases where the DNA sequence targeted for PCR amplification is at very low copy number the likelihood of a cross-link or adduct comprising each and every copy of the target DNA is a major concern. To maximize the chances of a successful PCR amplification it is necessary to limit the size of DNA fragments produced by the PCR amplification (amplicons) to the minimum necessary for analysis, to use only the most favored primer sequences producing such minimal amplicons, and to produce as many diagnostic amplicons from a single aliquot of target DNA as possible.

The requirement for such small amplicon size limits the number of choices for distributing primers along a target sequence and requires that multiple closely related priming sites be used to ensure that no single site is compromised by cross-linking or the presence of a disruptive adduct within the primer binding sequence. Because, DNA sequences are not entirely heterologous, and because optimal primer binding sites tend to favor higher G-C content, especially at the 3' end of the primer sequence, the best primers for generating a set of amplicons tend to cluster into narrow regions of a given target sequence. To ensure that each amplicon is produced specifically and solely from the desired primer pair usually each amplicon must be produced individually to avoid formation of primer dimers or recombinant amplification products produced during the PCR amplification process by cross hybridization of amplicon strands. Practically speaking, this requires that the target DNA be diluted among multiple PCR reactions which is an inefficient use of target DNA and is not practical with the tiny amount of bacterial DNA that can be recovered from FFPE biopsy samples. The more efficient method disclosed here involves segregating PCR primer pairs into mutually compatible pools such that there is minimal risk of primer-dimer formation or cross-hybridization between nascent amplicons during PCR amplification. This sort of segregational pooling of primer pairs allows efficient and automatable handling of FFPE samples containing rare DNA sequences to be analyzed by PCR-amplification-based methods in a clinical laboratory setting.

SUMMARY OF THE INVENTION

In one aspect the invention provides a set of PCR amplification primers for characterizing the presence of drug resistant *H. pylori* in FFPE preserved tissue. Primers consisting of two pairs of primers (one forward and one reverse in each pair) for separate genes characteristic of known drug resistant *H. pylori* strains are listed in FIG. 2. The example genes presented here include 16S rRNA (related to tetracycline resistance), 23S rRNA (related to clarithromycin resistance), pbp1 (related to resistance to penicillin antibiotics), gyrA (related to resistance to fluoroquinone antibiotics), rpoB (related to rifabutin resistance) and rdxA (involved in resistance to metronidazole). Those skilled in the art understand that other genetic loci involved in resistance to other antibiotics are known and may be included in or substituted for those described here. Practically, use of two primer pairs for each target gene minimizes the chance that any particular lesion (such as a cross-link or adduct) found in the target DNA sequences will inhibit PCR amplification from both amplicons, since such lesions are unlikely to occur at two different primer binding sites and involve all copies of the target gene within the target (template) DNA. However, the use of two pairs of primers targeting the same region of the bacterial chromosome, yet producing different but overlapping fragments requires that the PCR amplification reactions be carried out separately in order to avoid producing hybrid amplicons that do not match the full length amplicons each primer pair is designed to produce. Thus, at least two PCR amplification reactions must be performed for each set of primer pairs. In contrast, PCR primer pairs targeting different genes and producing amplicons with no homologous sequences can be pooled and thus the limited amount of target bacterial DNA that can be amplified from FFPE-preserved tissue used as efficiently as possible. The invention teaches segregation of primer pairs targeting an overlapping set of amplicons into separate pools and performing a single PCR amplification reaction on the segregated pools to produce the desired amplicons. In one example presented here, as many as 10 amplicons diagnostic for the five different types of drug resistant *H. pylori* genes listed above can be produced from just two PCR reactions using DNA extracted from FFPE gastric biopsy samples.

One embodiment of the invention is a method for detecting within a sample mutations in a plurality of genes, the method comprising a) identifying PCR primer pairs suitable for producing amplicons comprising regions of each of the genes containing one or more mutations, b) segregating PCR primer pairs comprising one or more primers that interfere with amplicon generation by another PCR primer pair into separate PCR primer pair pools, wherein each of the separate PCR primer pair pools contain a plurality of PCR primer pairs; c) generating amplicons from each of the separate PCR primer pair pools and target DNA isolated from the sample; d) combining all amplicons produced from each of the separate PCR primer pair pools and the target DNA into a sample amplicon pool, adding a unique index sequence to the amplicons within the sample amplicon pool to generate an indexed sample amplicon pool, optionally further combining the indexed sample amplicon pool with one or more differentially indexed sample amplicon pools from different samples, and sequencing all indexed sample amplicons simultaneously; and e) identifying mutations within the indexed sequenced amplicons from a sample by reference to corresponding wild-type gene sequences.

In one embodiment of the invention, the sample is a biopsy sample and, in another embodiment, the biopsy is a gastric biopsy. In a further embodiment, the biopsy sample comprises a formalin-fixed paraffin embedden biopsy sample. In another embodiment, the sample contains *Helicobacter pylori* (*H. pylori*).

In another embodiment, the plurality of genes comprises genes selected from the group consisting of *H. pylori* 16S rRNA, 23S rRNA, gyrA, rpoB, pbp1, and rdxA. In further embodiments, the identified mutation is an A2142G, A2143G, and/or A2142C mutation of the *H. pylori* 23S rRNA gene; an A928C, AG926-927GT, A926G/A928C and/or AGA926-928TTC mutation of the *H. pylori* 16S rRNA gene; a C261A, C261G, G271A, and/or G271T mutation of the *H. pylori* gyrA gene encoding DNA gyrase subunit A; between codons 525 and 545 of the *H. pylori* rpoB gene encoding the beta/beta' subunit of DNA-directed RNA polymerase; a C1242A or C1242G mutation in the *H. pylori* pbp1 gene encoding penicillin-binding protein 1; or within the *H. pylori* rdxA gene. In another embodiment, the identified mutation produces a loss of function of *H. pylori* oxygen-insensitive (Type I) NAPD(P)H nitroreductase encoded by rdxA.

In one embodiment of the invention, the amplicons do not exceed 230 base pairs in length. In another embodiment, the amplicons are greater than 130 base pairs in length. In a further embodiment, the PCR primer pair comprising one or more primers that interfere with amplicon generation by another PCR primer pair interfere by forming cross pair primer-dimers or by forming cross pair truncated amplicons.

Another embodiment of the invention is directed to a method for detecting within a patient derived sample the presence of drug resistant *H. pylori*, the method comprising: a) generating amplicons from DNA isolated from the patient derived sample and; i) PCR primer pair pool 1 comprising primers SEQ ID NOs. 1-10; ii) PCR primer pair pool 2 comprising primers SEQ ID Nos. 11-22; iii) PCR primer pair pool 3 comprising primers SEQ ID Nos. 23-28; iv) PCR primer pair pool 4 comprising primers SEQ ID Nos. 29-32; v) PCR primer pair pool 5 comprising primers SEQ ID Nos. 33-38; vi) PCR primer pair pool 6 comprising primers SEQ ID Nos. 39-44; b) combining all amplicons produced from PCR primer pair pools 1-6 in step a) into a sample amplicon pool, adding a unique index sequence to the amplicons within the sample amplicon pool to generate an indexed sample amplicon pool, optionally further combining the indexed sample amplicon pool with one or more differentially indexed sample amplicon pools from different patient derived samples, and sequencing all indexed sample amplicons simultaneously; c) identifying mutations within the sequenced indexed sample amplicons by reference to SEQ ID Nos. 47-51, and d) determining the drug-resistant profile of *H. pylori* present in the patient-derived profile by the presence or absence of mutations identified in step c).

Yet another embodiment of the invention is directed to a method for detecting within a patient derived sample the presence of drug resistant *H. pylori*, the method comprising: a) generating amplicons from DNA isolated from the patient derived sample and; i) PCR primer pair pool 1 comprising primers SEQ ID Nos. 23-28; ii) PCR primer pair pool 2 comprising primers SEQ ID Nos. 29-32; iii) PCR primer pair pool 3 comprising primers SEQ ID Nos. 33-38; iv) PCR primer pair pool 4 comprising primers SEQ ID Nos. 39-44; b) combining all amplicons produced from PCR primer pair pools 1-4 in step a) into a sample amplicon pool, adding a unique index sequence to the amplicons within the sample amplicon pool to generate an indexed sample amplicon pool, optionally further combining the indexed sample amplicon pool with one or more differentially indexed sample amplicon pools from different patient derived samples, and sequencing all indexed sample amplicons simultaneously; c) identifying mutations within the sequenced indexed sample amplicons by reference to SEQ ID Nos. 47-51; and d) determining the drug-resistant profile of *H. pylori* present in the patient-derived profile by the presence or absence of mutations identified in step c).

In a further embodiment any of the amplicon pools described here can be sequenced by classical Sanger sequencing methods using one of the terminal primers to a single amplicon within the pool as a forward sequencing primer and the other terminal primer to that amplicon as a reverse sequencing primer. Alternatively, unique sequencing primers specific to each desired reaction for each individual amplicon within the amplicon pool can be used for the same purpose. In this way each of the amplicons can be directly sequenced from an amplicon pool. The amplicon pool may or may not be combined with other amplicon pools from the same FFPE extracted biopsy sample and the combined amplicons prepared for sequencing by addition of adaptors and indexing tags in preparation for Next Generation sequencing (NGS). Tagged amplicon pools derived from a single FFPE biopsy sample can be further combined with differentially tagged amplicon pools from different FFPE biopsy samples and the combined sample amplicon pools directly sequenced by high-throughput multiplex sequencing methods.

DESCRIPTION OF THE DRAWINGS

FIG. 2 is a table of the individual primers disclosed in the Descriptions and Examples.

FIG. 5 is a summary data table of 16 FFPE samples analyzed by Next Generation Sequencing (NGS) data from 16 FFPE samples using the segregational pooling and pooled amplicon strategy with mutations in each of six different genes characteristic of drug-resistant *H. pylori* identified. All mutations identified by NGS were confirmed by Sanger sequencing.

FIG. 6 is a summary data table of 24 FFPE samples analyzed by NGS data from 24 FFPE samples using the segregational pooling and pooled amplicon strategy with mutation in each of six different genes characteristic of drug-resistant *H. pylori* identified. The data table lists the gene mutations identified by NGS as well as their mutation frequency.

DETAILED DESCRIPTION OF THE INVENTION

Figure 1:
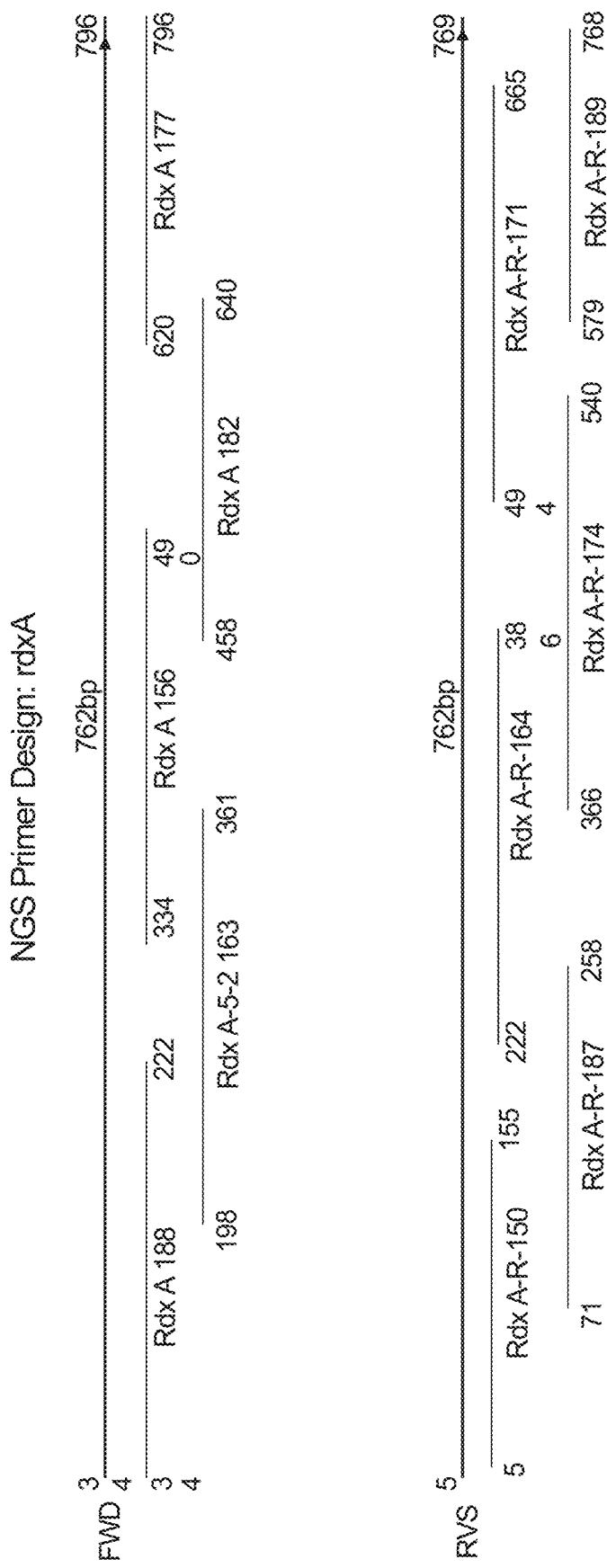
FIG. 1 depicts the *H. pylori* rdxA gene and illustrates the relative arrangement of the described amplicons.

The present invention provides methods and compositions for amplifying trace DNA sequences present in FFPE biopsy samples. These methods and compositions are useful for determining the presence of and characterizing the drug and multi-drug resistance profiles of *H. pylori* from FFPE gastric biopsy samples.

The methods and compositions described herein are directed to generating amplicons from trace bacterial DNA present in FFPE biopsy samples. Such DNA is especially subject to damage and PCR amplification of damaged DNA requires special steps to ensure that the desired sequences are amplified from the target DNA. These steps include minimizing the length of each amplicon recovered from the amplification reactions, determining the optimal primer sequences within the targeted DNA sequence, and strategically pooling overlapping amplicons and primers to avoid interference with one another. A process referred to as segregational pooling. In a typical PCR amplification scheme, where DNA integrity can be assumed to be relatively high, primer selection is not as limited as it is when the template DNA is known to be damaged by cross-linking or the presence of base adducts, as with FFPE derived DNA. Furthermore, the absolute levels of bacterial DNA that are found in typical biopsy samples are many orders of magnitude lower than the DNA of the host organism. This means that the sequences that are targeted for amplification are a minority of the total DNA in the sample and successfully amplifying one or more amplicons from such rare DNA sequences requires the most optimal primers and the most efficient use of the target DNA possible. Furthermore, to be generally useful in the commercial clinical laboratory, such methods should be compatible with and make use of established techniques and reagents to the greatest extent possible.

Total DNA was extracted from FFPE gastric biopsy samples using the Qiagen QIAamp DSP DNA FFPE Tissue Kit (Qiagen, Cat. No. 60404) following the manufacturer's instructions. Briefly, five 5 µm thick sections of a single FFPE biopsy sample were placed in a single tube and de-paraffinized with xylene, treated with proteinase K at 65° C. for one hour to lyse the cells within the de-paraffinized samples, and then held at 90° C. for an additional hour to de-cross-link cellular structures and to denature proteinase K. The de-paraffinized and lysed samples are cooled to room temperature applied to MiniElute PCR Purification column (Qiagen, Cat. No. 28004) following the manufacturers recommended procedure. The MiniElute column is washed twice and the DNA recovered from the FFPE biopsy sample recovered from the column with elution buffer. The recovered DNA was quantified with a Qubit 2.0 fluorometer (Thermo Fisher Scientific) and the DNA purity determined with a Nanodrop instrument (Thermo Fisher Scientific).

To verify the presence of *H. pylori* sequences within the total DNA samples from each biopsy sample, PCR amplification of a specific 125 base-pair fragment unique highly conserved region of the 23S rRNA gene of *H. pylori* was performed using PCR primers SEQ ID Nos: 45 and 46. The PCR product was purified and sequenced and confirmed to be specific to *H. pylori* by BLAST analysis [Altschul, S. F., Gish, W., Miller, W., Myers, E. W. & Lipman, D. J. (1990) "Basic local alignment search tool." J. Mol. Biol. 215:403-410]. The absence of the correct amplified product (amplicon) indicated no usable *H. pylori* DNA was present in the sample.

Samples that did produce the 125 base-pair *H. pylori* specific PCR amplicon were further investigated to determine the quality of the recovered DNA. To determine the suitability of the extracted DNA from FFPE gastric biopsy samples containing *H. pylori* for PCR amplification and sequencing, a multiplex PCR qualification assay was developed. This qualification assay involves PCR amplification of the human GAPDH gene encoding glyceraldehyde-3-phosphate dehydrogenase with a set of PCR primers capable of producing an amplicon ladder of 100, 200, 300, 400 and 500 base-pair fragments. FFPE DNA with no significant damage, with large fragment sizes and at relatively high concentration produces all five "rungs" of the amplicon ladder, whereas highly damaged and significantly fragmented DNA will not produce any of the expected amplicons. With our accumulated experience with this method, we rate DNA recovered from FFPE gastric biopsy samples as good if this test produces 2 to 5 bands of the amplicon ladder, intermediate if it produces only a single band, and poor if no bands are observed at all. The overall frequency of the number of amplicon bands observed across numerous FFPE extracted biopsy samples indicates that limiting analytical amplicon size to about 200 base-pairs or less provides the best balance between producing as much contiguous sequence as possible and avoiding PCR amplification terminating damage in the template DNA.

PCR amplification reactions using both freshly prepared or frozen *H. pylori* chromosomal DNA (as a positive control) and samples extracted from FFPE gastric biopsy samples (experimental samples) were performed with 1 U of Taq DNA Polymerase, 10 mM dNTP mix in a 100 mM Tris-HCl, 500 mM KCl and 25 mM MgCl2 buffer.

For samples analyzed by Sanger sequencing methods the PCR primers in FIG. 1 (SEQ ID NOs 1-44) were used as indicated with the thermal cycling parameters are: initial denaturing at 95° C. for 10 minutes, followed by 35 cycles of 30 seconds at 95° C., 30 seconds at 55° C. and 30 seconds at 72° C., then a final extension at 72° C. for 10 minutes. The resulting amplicons from each amplification reaction were purified with a MiniElute PCR Purification column following the manufacturer's instructions.

The purified amplicons were processed for Sanger sequencing with the BigDye Terminator v3.1 Cycle Sequencing Kit (Applied Biosystems, Cat. No. 4337455) following the manufacturer's protocol. The PCR sequencing reaction was executed with the following thermal parameters: 95° C. for 1 minute, then 25 cycles of 95° C. for 30 seconds, 56° C. for 30 seconds and 60° C. for 1 minute. The primer extension reactions were processed with the Agencourt CleanSEQ kit (Beckman Coulter Life Sciences Cat. No. A29151) following the manufacturer's instructions. Samples were loaded and analyzed on an ABI 3500 Genetic Analyzer (Applied Biosystems). Raw sequence data was collected with 3500 Series Data Collection Software (Applied Biosystems) and assembled and aligned against reference sequences using Sequencher v 5.4 software (Gene Codes Corp.).

In the case of samples destined for NGS sequencing the Illumina overhang adapter sequence is added to the locus-specific primer sequences listed in FIG. 2 (SEQ ID NOs 1-44). The forward overhang sequence (added to the 5' side of the locus specific forward primer sequence) is TCGTCGGCAGCGTCAGATGTGTAT-AAGAGACAG (SEQ ID NO. 47) and the reverse overhang sequence (added to the 5' side of the locus specific reverse primer sequence) is GTCTCGTGGGCTCGGAG-ATGTGTATAAGA-GACAG (SEQ ID NO. 48). The first round PCR amplification thermal cycling parameters are: initial denaturing at 95° C. for 11 minutes, followed by 35 cycles of 30 seconds at 95° C., 1 minute at 59° C. and 1 minute at 72° C., then a final extension at 72° C. for 10 minutes. Second stage PCR reactions (involving addition of multiplex index adapters) involved thermal cycling parameters: 98° C. for 30 seconds, 17 cycles of 98° C. for 20 seconds, 60° C. for 30 seconds and 72° C. for 45 seconds and a final extension at 72° C. for 5 minutes. The libraries were then processed with the Agencourt AMPure XP kit (Beckman Coulter Life Sciences Cat. No. A63880) following the manufacturer's instructions, quantitated on a 2100 BioAnalyzer (Agilent Technologies) diluted as necessary and loaded onto the Illumina MiSeq sequencing instrument (Illumina, Inc.). Data analysis was performed using NextGENe V 2.4.1.1 software (SoftGenetics).

The present invention is illustrated in the following Examples, which are set forth to aid in understanding the invention, but should not be construed to limit in any way the scope of the invention as defined in the claims that follow.

Example 1

Segregational Pooling of PCR Primers and Amplicons to Characterize Drug Resistance from Multiple Genetic Loci In one aspect of the invention, multiple loci encoding different forms of drug-resistance can be simultaneously characterized by segregating the PCR primers used to generate the diagnostic amplicons covering each of the targeted loci. PCR primer pairs comprising SEQ ID NOs: 1 and 2 for producing a 168 base-pair amplicon (16SrRNA 168) spanning positions 926-928 of the 16S rRNA gene of *H. pylori*. Virtually any mutation in these positions produces a low level of tetracycline resistance, while the triple mutation AGA926-928TTC is associated with very high levels of tetracycline resistance. A second primer pair comprising SEQ ID NOs: 11 and 12 produce a 162 base-pair amplicon (16SrRNA 162) also encompassing positions 926-928 of the *H. pylori* 16S rRNA. Another PCR primer pair comprising SEQ ID NOs: 3 and 4 produces a 194 base pair amplicon (23SrRNA 194) spanning positions 2142 and 2143 of the 23S rRNA gene of *H. pylori*. Mutation of these positions, particularly A2142G, A2142C and A2143G mutations are associated with clarithromycin resistance. A second primer pair comprising SEQ ID NOs: 13 and 14 produces a 170 base-pair amplicon (23SrRNA 170) which also spans positions 2142 and 2143 of the *H. pylori* 23S rRNA. Another PCR primer pair comprising SEQ ID NOs: 5 and 6 produces a 193 base-pair amplicon (gyrA 193) which spans the region encoding amino acid positions 87 to 91 of the A subunit of *H. pylori* gyrase, encoded by the gyrA gene. Mutations of Asn87 to Lys or Tyr and mutation of Asp91 to Gly, Asn or Tyr, individually or together are known to produce resistance to fluoroquinone antibiotics. A second PCR primer pair spanning this region of the *H. pylori* gyrA gene, comprising SEQ ID NOs: 15 and 16 produces a 139 base-pair amplicon (gyrA 139). A third PCR primer pair spanning the same region comprising SEQ ID NOs: 17 and 18 produce a 137 base-pair amplicon (gyrA 137). Another PCR primer pair comprising SEQ ID NOs: 7 and 8 produce a 159 base-pair amplicon (pbpA 159) which encompasses the sequence encoding amino acid position 414 of the *H. pylori* pbp1 gene. Mutation of the serine normally found at position 414 of penicillin-binding protein 1 to an arginine produces resistance to amoxicillin and other penicillin antibiotics. Another PCR primer pair, SEQ ID NOs: 19 and 20 produce a 140 base-pair amplicon (pbpA 140) that also encompasses the sequence encoding position 414 of *H. pylori* penicillin-binding protein 1. Another PCR primer pair comprising SEQ ID NOs: 9 and 10 produce a 228 base-pair amplicon encompassing codons 525 to 545 of the *H. pylori* rpoB gene encoding the β/β' subunit of RNA polymerase. Mutation of any of the codons within this region can confer resistance to rifabutin and other rifamycin-like antibiotics. A PCR primer pair comprising SEQ ID NOs: 21 and 22 also produces an amplicon (rpoB-R-167) which is 167 base-pairs and encompasses the critical codons within rpoB.

Each pair of PCR primers targeting a particular gene region potentially encoding a drug-resistant mutation are segregated into separate PCR primer pair pools containing one or more unique primer pairs targeting different genes. Thus, PCR amplification of each pool produces amplicons specific to the plurality of genes within each pool and minimizes the chance of PCR amplification artifacts such as primer-dimers or cross pair amplicon truncation caused by homologous pairing within overlapping amplicon sequences. As shown in FIG. 2, pool 5GF comprises PCR primer pairs 16SrRNA 168, 23SrRNA 194, gyrA193, pbpA 159 and rpoB 228. When FFPE derived *H. pylori* target DNA is amplified with these primer pairs five unique amplicons of 159, 168, 193, 194 and 228 base-pairs are produced.

Amplicon pool 5GR (FIG. 2) comprises PCR primer pairs 16SrRNA 162R, 23SrRNA 170R, gyrA 139R, gyrA 137R, pbpA 140 and rpoB-R-167. When FFPE derived *H. pylori* target DNA is amplified with these primer pairs as many as 8 amplicons are produced. Four of these are unique amplicons of 140, 162, 167 and 170 base-pairs (corresponding to the pbpA-specific amplicon, 16S rRNA-specific amplicon, the rpoB-specific amplicon and the 23S rRNA-specific amplicon, respectively). The remaining four amplicons represent permutations of the two pairs of gyrA-specific PCR primer pairs present in pool 5GR. These primer pairs partially overlap one another in the same direction such that four possible amplicons can be produced from the two pairs of primers. Because the partial overlap of primers is limited to primers that have the same strand orientation (direction) there is no risk of primer-dimer formation, and because the amplified sequence between the primers is identical (except for the absolute length of the amplified sequence) no cross-hybridization between amplicons will produce new sequences. Thus, the two pairs of semi-unique primers can be accommodated within the amplicon pool. In this case, these primers may produce as many as four homologous amplicons of 131, 137, 139 and 145 base-pairs. The sequence of these amplicons is identical from end to end with the sequence in each of the other amplicons—with the exception of the few base-pairs missing from the ends of the shorter amplicons, which are present in the longer amplicons.

Figure 4:
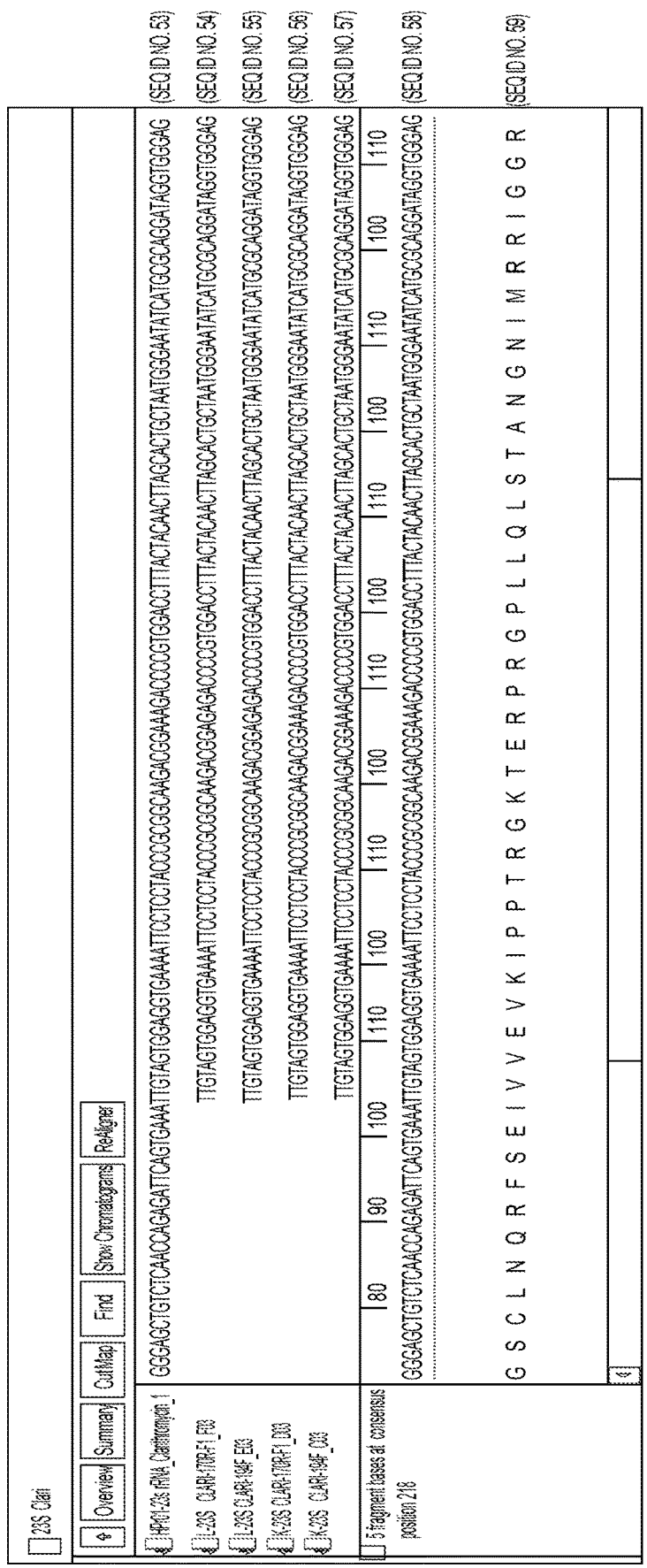
FIG. 4 identifies a representative mutation in 23S rRNA (in FFPE samples FFPE_K and L) 23 S rRNA Clarithromycin sequences alignment sequenced with 23S rRNA 194-F and 170R-F. The red box shows the mutation loci on 23S rRNA

Alignment of each of the sequenced amplicons allows identification of mutations conferring drug resistance. FIG. 4 is an example of the A2142G mutation in the 23S rRNA identified in two independent FFPE derived sample ("E" and "K") that indicates that treatment of the *H. pylori* strains afflicting the patients from whom these samples were derived is unlikely to respond to clarithromycin. The top sequence is a known clarithromycin resistant strain of *H. pylori* while the two sequences immediately below the control are independent PCR amplicons from sample "E" and the last two sequences are independent amplicons from sample "F".

Example 2

Segregational Pooling of PCR Primers and Amplicons to Characterize Drug Resistance Derived from Surveying the Entire Coding Sequence of a Gene In another aspect of the invention, segregated PCR primer pools allow efficient coverage of an entire gene. Resistance to metronidazole can occur as a result of any loss of function mutation in the *H. pylori* rdxA gene encoding the bacterial oxygen-insensitive (Type I) NAD(P)H nitroreductase. Metronidazole is activated by the action of this enzyme and thus, any frameshift, or point mutation within the rdxA gene encoding this enzyme has the potential to confer resistance to metronidazole. Unlike the previously described embodiments, no single short amplicon can encompass the known mutational spectrum of metronidazole resistance encountered in *H. pylori*. To address this problem, two series of PCR primer pairs producing overlapping amplicons were designed such that the primers within each series produce short amplicons that together cover the entire coding region of the rdxA gene. The primers between the two series are located in unique positions, but some may be within the coding sequence of the rdxA gene offset by only a few bases in one direction relative to the analogous primers in the other series (in a manner similar to the partially overlapping gyrA primers within amplicon pool 5GR described in the previous paragraph). This strategy reduces the chance of a single cross-link or adduct present in the target DNA from entirely blocking production of an amplicon. The sequence derived from amplicons produced by one series of PCR primers can be assembled with amplicons produced from the other series of PCR primers to ensure that complete coverage of the rdxA gene is achieved from the total set of primer pools. Each series of primers is placed into one of two amplicon pools for each series so that amplicons within the series that may overlap and which are produced from primers that are prone to form primer-dimers are segregated into separate pools. In the case of the *H. pylori* rdxA gene, one series of five short amplicons collectively span the entire rdxA coding sequence. These five amplicons, from 5' to 3' comprise the rdxA 188 amplicon (produced from PCR primer pair SEQ ID NOs: 23 and 24), the rdxA-5-2-163 amplicon (produced from PCR primer pair SEQ ID NOs: 29 and 30), the rdxA 156 amplicon (produced from PCR primer pair SEQ ID NOs: 25 and 26), the rdxA 182 amplicon (produced from PCR primer pair SEQ ID NOs: 31 and 32) and the rdxA 177 amplicon (produced from PCR primer pair SEQ ID NOs: 27 and 28). Within this series PCR primer pairs producing amplicons rdxA 188, rdxA156 and rdxA 177 are placed into a single pool designated rdxA-F1, while PCR primer pairs producing amplicons rdxA-5-2-163 and rdxA 182 are combined into a different pool designated rdxA-F2 (FIG. 2). In another series six short amplicons are used to span the entire *H. pylori* rdxA gene. These amplicons, arrayed 5' to 3' comprise the rdxA-R-150 amplicon (produced from PCR primer pair SEQ ID NOs: 33 and 34), the rdxA-R-187 amplicon (produced from PCR primer pair SEQ ID NOs: 39 and 40), the rdxA-R-164 amplicon (produced from PCR primer pair SEQ ID NOs: 35 and 36), the rdxA-R0174 amplicon (produced from PCR primer pair SEQ ID NOs: 41 and 42, the rdxA-R-171 amplicon (produced from PCR primer pair SEQ ID NOs: 37 and 38) and the rdxA-R-189 amplicon (produced from PCR primer pair SEQ ID NOs: 43 and 44). Within this series PCR primer pairs producing amplicons rdxA-R-150, rdxA-R-164 and rdxA-R-171 are combined into one pool designated rdxA-R1, while PCR primer pairs producing amplicons rdxA-R-187, rdxA-R-174 and rdxA-R-189 are combined into a different pool designated rdxA-R2 (FIG. 2). These PCR primer pools are used to generate their cognate amplicons from *H. pylori* DNA extracted from FFPE biopsy samples. Depending on how the amplicons are to be sequenced amplicons from each PCR reaction may be further combined so that each series is represented by a single amplicon pool.

Figure 3:
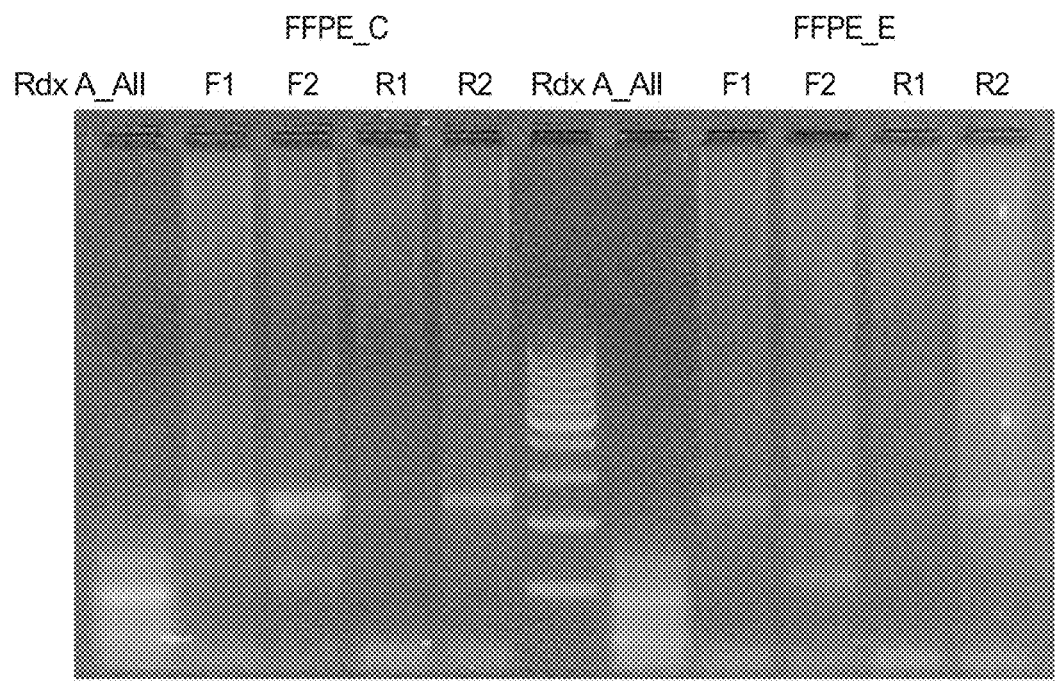
FIG. 3 is an electrophoresis gel demonstrating that pooling all rdxA specific primers generates incorrect sized amplicons, whereas the segregated primer pools described here generate correct sized amplicons.

As shown in FIG. 3 proper segregational pooling produces the correct (predicted) amplicons, whereas the same primers when present in a single pool produce a series of PCR products comprised of incorrect amplicons and primer dimers. Two FFPE samples. "FFPE_C" and "FFPE E" were processed as described and served as target DNA for analysis of the rdxA gene. Lane 6 (counting from the left-most lane as lane 1) is a double-stranded DNA size marker (Ready-to-Use 100 bp DNA Ladder, Biotium, Inc.). The size marker is flanked on each side by sample specific pooled amplification products. Lanes 1 and 7 labeled "RDX-All" are the result of PCR amplification reactions containing all the PCR primers of the amplicons spanning the entire rdxA gene described above. The lanes marked "F1" (lanes 2 and 8) correspond to the rdxA-F1 pool comprising the rdxA 188, rdxA156 and rdxA 177 amplicon primes and both sample lanes contain amplicons between 150 and 200 base-pairs as predicted. The lanes marked "F2" (lanes 3 and 9) correspond to the rdxA-F2 pool comprising the rdxA-5-2-163 and rdxA 182 amplicon primers and both sample lanes contain amplicons of the correct size. Note that a minor product of about 60 base-pairs is also present, however this amplicon does not interfere in sequencing the correct amplicons and likely represents a product of internal recombination within or between one of the desired amplicons. The lanes marked "R1" (lanes 4 and 10) correspond to the rdxA-R1 pool comprising the rdxA-R-150, rdxA-R-164 and rdxA-R-171 amplicon primers and the desired amplicons are clustered on the gel between 150 and around 170 base-pairs. The lanes marked "R2" (lanes 5 and 11) correspond to the rdxA-R2 pool comprising the rdxA-R-187, rdxA-R-174 and rdxA-R-189 amplicon primers produce the proper sized amplicons.

FIG. 5 illustrates the ability of the method to determine the presence and pattern of drug and multi-drug resistance in multiple isolates derived from FFPE samples based on a single NGS analysis. In this case, the 5 separate genes analyzed as described in Example 1, as well as the rdxA gene analyzed as described in Example 2 are collated into a single report outlining the potential resistance profile of *H. pylori* in each patient-derived FFPE biopsy sample to each of the six drugs.

FIG. 6 also illustrates the ability of the method to determine the presence and pattern of drug and multi-drug resistance in multiple isolates derived from FFPE samples based on NGS analysis as described in Examples 1 and 2. The table lists the genetic mutations found in each sample as well as the frequency of each mutation. The results show that NGS analysis can distinguish between FFPE samples that do not have any mutations versus those that do. For example, of the 24 samples, 10 (42%) had no mutations (Nos. 5, 6, 8, 9, 13, 17, and 21-24). However, the results also show that NGS analysis can detect both single and multiple mutations within one FFPE sample. For example, 14 samples (58%) had at least one gene mutation (Nos. 1-4, 7, 10-12, 14-16, and 18-20). Of these 14 samples, 11 samples had mutations in a single gene (Nos. 2, 4, 7, 11-12, 14-16, 18, 19, and 20) and 3 samples had mutations in multiple genes (Nos. 1, 3, and 10).

Of the samples with single gene mutations, 5 samples had gyrA gene mutations only (Nos. 2, 4, 15, 18, and 19), 2 samples had rdxA gene mutations only (Nos. 7 and 20), and 4 samples had 23S rRNA gene mutations only (Nos. 11, 12, 14, and 16). Of the samples with gyrA mutations only, one of the samples had two mutations with the gyrA gene (No. 19). As discussed above, the presence of gyrA gene mutations indicates fluoroquinone antibiotic resistance. Of the samples with rdxA gene mutations only, one of the samples had two mutations within the rdxA gene (No. 7). As discussed above, the presence of rdxA gene mutations indicates resistance to metronidazole.

The 3 samples with multiple gene mutations had mutations in both 23S rRNA and gyrA (Nos. 1 and 3) and both gyrA and rdxA (No. 10). The concurrent 23S rRNA and gyrA mutations indicate both clarithromycin and fluoroquinone antibiotic resistance; whereas, the concurrent gyrA and rdxA mutations indicate both fluoroquinone antibiotic resistance and metronidazole resistance.

What is claimed is:

1. A method for detecting within a *Helicobacter pylori* (*H. pylori*) sample mutations in a plurality of drug resistance genes, the method comprising:
   a) identifying PCR primer pairs suitable for producing amplicons comprising regions of each of the genes containing one or more mutations,
   b) segregating PCR primer pairs comprising one or more primers that interfere with amplicon generation by another PCR primer pair into separate PCR primer pair pools, wherein each of the separate PCR primer pair pools contains a plurality of PCR primer pairs;
   c) generating amplicons from each of the separate PCR primer pair pools and target DNA isolated from the sample;
   d) combining all amplicons produced from each of the separate PCR primer pair pools and the target DNA into a sample amplicon pool, adding a unique index sequence to the amplicons within the sample amplicon pool to generate an indexed sample amplicon pool, optionally further combining the indexed sample amplicon pool with one or more differentially indexed sample amplicon pools from different samples, and sequencing all indexed sample amplicons simultaneously; and
   e) identifying mutations within the indexed sequenced amplicons from a sample by reference to corresponding wild-type gene sequences,
   wherein amplicons diagnostic for at least three different types of drug resistance genes are produced from two PCR reactions in step (c); and
   wherein the PCR primer pair pools in step (b) contain:
   i) PCR primer pair pool 1 comprising primers SEQ ID NOs. 1-10;

ii) PCR primer pair pool 2 comprising primers SEQ ID NOs. 11-22;
iii) PCR primer pair pool 3 comprising primers SEQ ID NOs. 23-28;
iv) PCR primer pair pool 4 comprising primers SEQ ID NOs. 29-32;
v) PCR primer pair pool 5 comprising primers SEQ ID NOs. 33-38; and
vi) PCR primer pair pool 6 comprising primers SEQ ID NOs. 39-44.

2. The method of claim 1, wherein the sample is a biopsy sample.

3. The method of claim 2, wherein the biopsy is a gastric biopsy.

4. The method of claim 2, wherein the sample comprises a formalin-fixed paraffin embedded biopsy sample.

5. The method of claim 1, wherein the identified mutation is an A2142G, A2143G, and/or A2142C mutation of the *H. pylori* 23S rRNA gene.

6. The method of claim 1, wherein the identified mutation is an A928C, AG926-927GT, A926G/A928C and/or AGA926-928TTC mutation of the *H. pylori* 16S rRNA gene.

7. The method of claim 1, wherein the identified mutation is a C261A, C261G, G271A, and/or G271T mutation of the *H. pylori* gyrA gene encoding DNA gyrase subunit A.

8. The method of claim 1, wherein the identified mutation is between codons 525 and 545 of the *H. pylori* rpoB gene encoding the beta/beta' subunit of DNA-directed RNA polymerase.

9. The method of claim 1, wherein the identified mutation is a C1242A or C1242G mutation in the *H. pylori* pbp1 gene encoding penicillin-binding protein 1.

10. The method of claim 1, wherein the identified mutation is within the *H. pylori* rdxA gene.

11. The method of claim 10, wherein the identified mutation produces a loss of function of *H. pylori* oxygen-insensitive (Type I) NAPD(P)H nitroreductase encoded by rdxA.

12. The method of claim 1, wherein the amplicons do not exceed 230 base pairs in length.

13. The method of claim 1, wherein the amplicons are greater than 130 base pairs in length.

14. The method of claim 1 wherein the PCR primer pairs in step (b) comprising one or more primers that interfere with amplicon generation by another PCR primer pair interfere by forming cross pair primer-dimers.

15. The method of claim 1, wherein the PCR primer pairs in step (b) comprising one or more primers that interfere with amplicon generation by another PCR primer pair interfere by forming cross pair truncated amplicons.

16. A method for detecting within a patient derived sample the presence of drug resistant *H. pylori*, the method comprising:
    a) generating amplicons from DNA isolated from the patient derived sample and from PCR primer pair pools containing:
        i) PCR primer pair pool 1 comprising primers SEQ ID NOs. 1-10;
        ii) PCR primer pair pool 2 comprising primers SEQ ID NOs. 11-22;
        iii) PCR primer pair pool 3 comprising primers SEQ ID NOs. 23-28;
        iv) PCR primer pair pool 4 comprising primers SEQ ID NOs. 29-32;
        v) PCR primer pair pool 5 comprising primers SEQ ID NOs. 33-38; and
        vi) PCR primer pair pool 6 comprising primers SEQ ID NOs. 39-44;
    b) combining all amplicons produced from the PCR primer pair pools 1-6 in step a) into a sample amplicon pool, adding a unique index sequence to the amplicons within the sample amplicon pool to generate an indexed sample amplicon pool, optionally further combining the indexed sample amplicon pool with one or more differentially indexed sample amplicon pools from different patient derived samples, and sequencing all indexed sample amplicons simultaneously;
    c) identifying mutations within the sequenced indexed sample amplicons by reference to SEQ ID Nos. 47-51; and
    d) determining the drug-resistant profile of *H. pylori* present in the patient-derived profile by the presence or absence of mutations identified in step c).

* * * * *

SEQUENCE LISTING

<160> NUMBER OF SEQ ID NOS: 59

<210> SEQ ID NO 1
<211> LENGTH: 17
<212> TYPE: DNA
<213> ORGANISM: Artificial Sequence
<220> FEATURE:
<223> OTHER INFORMATION: PCR primer

<400> SEQUENCE: 1
taacgcatta agcatcc                                                  17

<210> SEQ ID NO 2
<211> LENGTH: 18
<212> TYPE: DNA
<213> ORGANISM: Artificial Sequence
<220> FEATURE:
<223> OTHER INFORMATION: PCR primer

<400> SEQUENCE: 2
ccagacactc cactattt                                                  18

<210> SEQ ID NO 3
<211> LENGTH: 15
<212> TYPE: DNA
<213> ORGANISM: Artificial Sequence
<220> FEATURE:
<223> OTHER INFORMATION: PCR primer

<400> SEQUENCE: 3
ccgacctgca tgaat                                                     15

<210> SEQ ID NO 4
<211> LENGTH: 15
<212> TYPE: DNA
<213> ORGANISM: Artificial Sequence
<220> FEATURE:
<223> OTHER INFORMATION: PCR primer

<400> SEQUENCE: 4
agccaaagcc cttac                                                     15

<210> SEQ ID NO 5
<211> LENGTH: 19
<212> TYPE: DNA
<213> ORGANISM: Artificial Sequence
<220> FEATURE:
<223> OTHER INFORMATION: PCR primer

<400> SEQUENCE: 5
tatgcgatgc atgaattag                                                 19

<210> SEQ ID NO 6
<211> LENGTH: 19
<212> TYPE: DNA
<213> ORGANISM: Artificial Sequence
<220> FEATURE:
<223> OTHER INFORMATION: PCR primer

<400> SEQUENCE: 6
catcaataga gccaaagtt                                                 19

<210> SEQ ID NO 7
<211> LENGTH: 17
<212> TYPE: DNA
<213> ORGANISM: Artificial Sequence
<220> FEATURE:
<223> OTHER INFORMATION: PCR primer

<400> SEQUENCE: 7
ttgataatgg ctattcc                                                   17

<210> SEQ ID NO 8
<211> LENGTH: 15
<212> TYPE: DNA
<213> ORGANISM: Artificial Sequence
<220> FEATURE:
<223> OTHER INFORMATION: PCR primer

<400> SEQUENCE: 8
ggctcaaggc ttctt                                                     15

<210> SEQ ID NO 9
<211> LENGTH: 20

-continued

```
<212> TYPE: DNA
<213> ORGANISM: Artificial Sequence
<220> FEATURE:
<223> OTHER INFORMATION: PCR primer

<400> SEQUENCE: 9
gacaagctca ctaccatgag                                               20

<210> SEQ ID NO 10
<211> LENGTH: 18
<212> TYPE: DNA
<213> ORGANISM: Artificial Sequence
<220> FEATURE:
<223> OTHER INFORMATION: PCR primer

<400> SEQUENCE: 10
cacatccctg gcttcaaa                                                 18

<210> SEQ ID NO 11
<211> LENGTH: 17
<212> TYPE: DNA
<213> ORGANISM: Artificial Sequence
<220> FEATURE:
<223> OTHER INFORMATION: PCR primer

<400> SEQUENCE: 11
ctagcggatt ctctcaa                                                  17

<210> SEQ ID NO 12
<211> LENGTH: 17
<212> TYPE: DNA
<213> ORGANISM: Artificial Sequence
<220> FEATURE:
<223> OTHER INFORMATION: PCR primer

<400> SEQUENCE: 12
cagtaatgca gctaacg                                                  17

<210> SEQ ID NO 13
<211> LENGTH: 17
<212> TYPE: DNA
<213> ORGANISM: Artificial Sequence
<220> FEATURE:
<223> OTHER INFORMATION: PCR primer

<400> SEQUENCE: 13
catcaagggt ggtatct                                                  17

<210> SEQ ID NO 14
<211> LENGTH: 17
<212> TYPE: DNA
<213> ORGANISM: Artificial Sequence
<220> FEATURE:
<223> OTHER INFORMATION: PCR primer

<400> SEQUENCE: 14
ttgtagtgga ggtgaaa                                                  17

<210> SEQ ID NO 15
<211> LENGTH: 18
<212> TYPE: DNA
<213> ORGANISM: Artificial Sequence
<220> FEATURE:
<223> OTHER INFORMATION: PCR primer

<400> SEQUENCE: 15
```

```
cgttatcgcc atcaatag                                                     18

<210> SEQ ID NO 16
<211> LENGTH: 19
<212> TYPE: DNA
<213> ORGANISM: Artificial Sequence
<220> FEATURE:
<223> OTHER INFORMATION: PCR primer

<400> SEQUENCE: 16
ggtgatgtga ttggtaaat                                                    19

<210> SEQ ID NO 17
<211> LENGTH: 18
<212> TYPE: DNA
<213> ORGANISM: Artificial Sequence
<220> FEATURE:
<223> OTHER INFORMATION: PCR primer

<400> SEQUENCE: 17
ccatcaatag agccaaag                                                     18

<210> SEQ ID NO 18
<211> LENGTH: 15
<212> TYPE: DNA
<213> ORGANISM: Artificial Sequence
<220> FEATURE:
<223> OTHER INFORMATION: PCR primer

<400> SEQUENCE: 18
atcgtgggtg atgtg                                                        15

<210> SEQ ID NO 19
<211> LENGTH: 17
<212> TYPE: DNA
<213> ORGANISM: Artificial Sequence
<220> FEATURE:
<223> OTHER INFORMATION: PCR primer

<400> SEQUENCE: 19
ttgataatgg ctattcc                                                      17

<210> SEQ ID NO 20
<211> LENGTH: 16
<212> TYPE: DNA
<213> ORGANISM: Artificial Sequence
<220> FEATURE:
<223> OTHER INFORMATION: PCR primer

<400> SEQUENCE: 20
ggttacaagc cctaaa                                                       16

<210> SEQ ID NO 21
<211> LENGTH: 20
<212> TYPE: DNA
<213> ORGANISM: Artificial Sequence
<220> FEATURE:
<223> OTHER INFORMATION: PCR primer

<400> SEQUENCE: 21
tgggacaaat tcggccataa                                                   20

<210> SEQ ID NO 22
<211> LENGTH: 17
<212> TYPE: DNA
<213> ORGANISM: Artificial Sequence
```

```
<220> FEATURE:
<223> OTHER INFORMATION: PCR primer

<400> SEQUENCE: 22
tttcatgggc ggtcagc                                                      17

<210> SEQ ID NO 23
<211> LENGTH: 22
<212> TYPE: DNA
<213> ORGANISM: Artificial Sequence
<220> FEATURE:
<223> OTHER INFORMATION: PCR primer

<400> SEQUENCE: 23
tggtaattgt ttcgttaggg at                                                22

<210> SEQ ID NO 24
<211> LENGTH: 18
<212> TYPE: DNA
<213> ORGANISM: Artificial Sequence
<220> FEATURE:
<223> OTHER INFORMATION: PCR primer

<400> SEQUENCE: 24
tggcgatttc agcgattt                                                     18

<210> SEQ ID NO 25
<211> LENGTH: 18
<212> TYPE: DNA
<213> ORGANISM: Artificial Sequence
<220> FEATURE:
<223> OTHER INFORMATION: PCR primer

<400> SEQUENCE: 25
aagcgcttca gcgttaat                                                     18

<210> SEQ ID NO 26
<211> LENGTH: 18
<212> TYPE: DNA
<213> ORGANISM: Artificial Sequence
<220> FEATURE:
<223> OTHER INFORMATION: PCR primer

<400> SEQUENCE: 26
tgcatgctgt ggttgaat                                                     18

<210> SEQ ID NO 27
<211> LENGTH: 24
<212> TYPE: DNA
<213> ORGANISM: Artificial Sequence
<220> FEATURE:
<223> OTHER INFORMATION: PCR primer

<400> SEQUENCE: 27
gaagagcgta tcaataagcc taaa                                              24

<210> SEQ ID NO 28
<211> LENGTH: 22
<212> TYPE: DNA
<213> ORGANISM: Artificial Sequence
<220> FEATURE:
<223> OTHER INFORMATION: PCR primer

<400> SEQUENCE: 28
atgccactcc ttgaacttta at                                                22
```

<210> SEQ ID NO 29
<211> LENGTH: 23
<212> TYPE: DNA
<213> ORGANISM: Artificial Sequence
<220> FEATURE:
<223> OTHER INFORMATION: PCR primer

<400> SEQUENCE: 29
agcctccaat aatgcaacta tcc                                          23

<210> SEQ ID NO 30
<211> LENGTH: 22
<212> TYPE: DNA
<213> ORGANISM: Artificial Sequence
<220> FEATURE:
<223> OTHER INFORMATION: PCR primer

<400> SEQUENCE: 30
cataccacca ttaacgctga ag                                           22

<210> SEQ ID NO 31
<211> LENGTH: 18
<212> TYPE: DNA
<213> ORGANISM: Artificial Sequence
<220> FEATURE:
<223> OTHER INFORMATION: PCR primer

<400> SEQUENCE: 31
atgcttggcg tgagattc                                                18

<210> SEQ ID NO 32
<211> LENGTH: 21
<212> TYPE: DNA
<213> ORGANISM: Artificial Sequence
<220> FEATURE:
<223> OTHER INFORMATION: PCR primer

<400> SEQUENCE: 32
ggcttattga tacgctcttc t                                            21

<210> SEQ ID NO 33
<211> LENGTH: 20
<212> TYPE: DNA
<213> ORGANISM: Artificial Sequence
<220> FEATURE:
<223> OTHER INFORMATION: PCR primer

<400> SEQUENCE: 33
atgccactcc ttgaacttta                                              20

<210> SEQ ID NO 34
<211> LENGTH: 18
<212> TYPE: DNA
<213> ORGANISM: Artificial Sequence
<220> FEATURE:
<223> OTHER INFORMATION: PCR primer

<400> SEQUENCE: 34
gcatgcttga tcgctttg                                                18

<210> SEQ ID NO 35
<211> LENGTH: 22
<212> TYPE: DNA
<213> ORGANISM: Artificial Sequence
<220> FEATURE:
<223> OTHER INFORMATION: PCR primer

<400> SEQUENCE: 35
atgcaactat ccaatcccat ta                                           22

<210> SEQ ID NO 36
<211> LENGTH: 24
<212> TYPE: DNA
<213> ORGANISM: Artificial Sequence
<220> FEATURE:
<223> OTHER INFORMATION: PCR primer

<400> SEQUENCE: 36
ccggagtctt ataaagttag agtg                                         24

<210> SEQ ID NO 37
<211> LENGTH: 18
<212> TYPE: DNA
<213> ORGANISM: Artificial Sequence
<220> FEATURE:
<223> OTHER INFORMATION: PCR primer

<400> SEQUENCE: 37
gtgcgctgca atttgttt                                                18

<210> SEQ ID NO 38
<211> LENGTH: 19
<212> TYPE: DNA
<213> ORGANISM: Artificial Sequence
<220> FEATURE:
<223> OTHER INFORMATION: PCR primer

<400> SEQUENCE: 38
ttaaacgagc gccattctt                                               19

<210> SEQ ID NO 39
<211> LENGTH: 21
<212> TYPE: DNA
<213> ORGANISM: Artificial Sequence
<220> FEATURE:
<223> OTHER INFORMATION: PCR primer

<400> SEQUENCE: 39
caaccaagta atcgcatcaa c                                            21

<210> SEQ ID NO 40
<211> LENGTH: 18
<212> TYPE: DNA
<213> ORGANISM: Artificial Sequence
<220> FEATURE:
<223> OTHER INFORMATION: PCR primer

<400> SEQUENCE: 40
catgggcgtg agcttaat                                                18

<210> SEQ ID NO 41
<211> LENGTH: 25
<212> TYPE: DNA
<213> ORGANISM: Artificial Sequence
<220> FEATURE:
<223> OTHER INFORMATION: PCR primer

<400> SEQUENCE: 41
ctaactttat aagactccgg ataga                                        25

<210> SEQ ID NO 42

```
<211> LENGTH: 22
<212> TYPE: DNA
<213> ORGANISM: Artificial Sequence
<220> FEATURE:
<223> OTHER INFORMATION: PCR primer

<400> SEQUENCE: 42
tgtgatggtt actgataagg at                                              22

<210> SEQ ID NO 43
<211> LENGTH: 19
<212> TYPE: DNA
<213> ORGANISM: Artificial Sequence
<220> FEATURE:
<223> OTHER INFORMATION: PCR primers

<400> SEQUENCE: 43
ctggcgattt cagcgattt                                                  19

<210> SEQ ID NO 44
<211> LENGTH: 22
<212> TYPE: DNA
<213> ORGANISM: Artificial Sequence
<220> FEATURE:
<223> OTHER INFORMATION: PCR primer

<400> SEQUENCE: 44
tggtaattgt ttcgttaggg at                                              22

<210> SEQ ID NO 45
<211> LENGTH: 22
<212> TYPE: DNA
<213> ORGANISM: Artificial Sequence
<220> FEATURE:
<223> OTHER INFORMATION: PCR primer

<400> SEQUENCE: 45
acaacccaga ctaccaaata ag                                              22

<210> SEQ ID NO 46
<211> LENGTH: 19
<212> TYPE: DNA
<213> ORGANISM: Artificial Sequence
<220> FEATURE:
<223> OTHER INFORMATION: PCR primer

<400> SEQUENCE: 46
gtgagctgtt acgctttct                                                  19

<210> SEQ ID NO 47
<211> LENGTH: 500
<212> TYPE: DNA
<213> ORGANISM: Helicobacter pylori

<400> SEQUENCE: 47
gtaatccgta gagatcaaga ggaatactca ttgcgaggcg acctgctgga acattactga     60
cgctgattgc gcgaaagcgt ggggagcaaa caggattaga taccctggta gtccacgccc    120
taaacgatgg atgctagttg ttggagggct tagttttcca gtaatgcagc taacgcatta    180
agcatcccgc ctggggagta cggtcgcaag attaaaatca aggaataga cggggacccg     240 cacaagcggt ggagcatgtg gtttaattcg aagatacacg aagaacctta cctaggcttg    300
acattgagag aatccgctag aaatagtgga gtgtctggct tgccagacct tgaaaacagg    360
tgctgcacgg ctgtcgtcag ctcgtgtcgt gagatgttgg gttaagtccc gcaacgagcg    420
```

```
caaccccttt tcttagttgc taacaggtta tgctgagaac tctaaggata ctgcctccgt    480
aaggaggagg aagtgggga                                                500

<210> SEQ ID NO 48
<211> LENGTH: 1500
<212> TYPE: DNA
<213> ORGANISM: Helicobacter pylori

<400> SEQUENCE: 48
caagtgataa taaaagggg tagagccctg attgggctag gctgctcgc cgcggtacca     60 aaccctatca aacttcgaat acctttatc gtatcttggg agtcaggcgg tgggtgataa   120
aatcaatcgt caaaggga acaacccaga ctaccaaata aggtccctaa gttctattct   180
gagtggaaaa agatgtgtgg ctactcaaac aaccaggagg ttggcttaga agcagccatc   240 cttaaagaa agcgtaacag ctcactggtc tagtggtcat gcgctgaaaa tataacgggg   300
ctaagataga caccgaattt gtagattgtg ttaaacacag tggtagaaga gcgttcatac   360
cagcgttgaa ggtataccgg taaggagtgc tggagcggta tgaagtgagc atgcaggaat   420
gagtaacgat aagatatatg agaattgtat ccgccgtaaa tctaaggttt cctacgcgat   480
ggtcgtcatc gtagggttag tcgggtccta agccgagtcc gaaaggggta ggtgatggca   540
aattggttaa tattccaata ccgactgtgg agcgtgatgg ggggacgcat agggttaagc   600
gagctagctg atggaagcgc tagtctaagg gcgtagattg gagggaaggc aaatccacct   660
ctgtatttga aacccaaaca ggctctttga gtccttttag gacaaaggga gaatcgctga   720
taccgtcgtg ccaagaaaag tctctaagca tatccatagt cgtccgtacc gcaaaccgac   780
acaggtagat gagatgagta ttctaaggcg cgtgaaagaa ctctggttaa ggaactctgc   840
aaactagcac cgtaagttcg cgataaggtg tgccacagcg atgtggtctc agcaaagagt   900
ccctcccgac tgtttaccaa aaacacagca ctttgccaac tcgtaagagg aagtataagg   960
tgtgacgcct gcccggtgct cgaaggttaa gaggatgcgt cagtcgcaag atgaagcgtt  1020
gaattgaagc ccgagtaaac ggcggccgta actataacgg tcctaaggta gcgaaattcc  1080
ttgtcggtta ataccgacc tgcatgaatg gcgtaacgag atgggagctg tctcaaccag  1140
agattcagtg aaattgtagt ggaggtgaaa attcctccta cccgcggcaa gacggaaaga  1200
ccccgtggac ctttactaca acttagcact gctaatggga atatcatgcg caggataggt  1260
gggaggcttt gaagtaaggg ctttggctct tatggagcca tccttgagat accacccttg  1320
atgtttctgt tagctaactg gcctgtgtta tccacaggca ggacaatgct tggtgggtag  1380
tttgactggg gcggtcgcct cctaaaaagt aacggaggct tgcaaaggtt ggctcattgc  1440
ggttggaaat cgcaagttga gtgtaatggc acaagccagc ctgactgtaa gacatacaag  1500

<210> SEQ ID NO 49
<211> LENGTH: 550
<212> TYPE: DNA
<213> ORGANISM: Helicobacter pylori

<400> SEQUENCE: 49
atgcaagata attcagtcaa tgaaacaaaa atatttgtag aagtggggat tgattcttct     60
attgaagaga gctatttagc ttattccatg agcgtgatca tagggcgcgc tttaccggac   120
gctagagatg gcttaaagcc cgtgcatagg cgtattttgt atgcgatgca tgaattaggc   180
cttacttcaa aagtcgctta caaaaaaagc gctaggatcg tgggtgatgt gattggtaaa   240
```

| | |
|---|---:|
| taccacccc atggcgataa tgcggtttat gatgcgctag tgagaatggc gcaagatttt | 300 |
| tccatgcgtt tggaattagt ggatgggcag ggcaactttg gctctattga tggcgataac | 360 |
| gccgcagcga tgcgttacac tgaagccaga atgactaagg cgagtgaaga aattttaagg | 420 |
| gatattgata agacaccat tgattttgtg cctaattatg acgataccct aaaagagcca | 480 |
| gatattttac caagccgtct gcctaacctt ttagtcaatg gggctaatgg gatcgctgtg | 540 |
| gggatggcga | 550 |

```
<210> SEQ ID NO 50
<211> LENGTH: 500
<212> TYPE: DNA
<213> ORGANISM: Helicobacter pylori

<400> SEQUENCE: 50
```

| | |
|---|---:|
| aactaacgcg tctaatgaag atgaagacaa cttaaacgct agcatgatcg ttacagacac | 60 |
| gagcaccggt aagattttag ctttagtggg ggggattgat tataaaaaaa gcgctttcaa | 120 |
| tcgcgccacg caagccaaac ggcagtttgg gagcgcgata aagccttttg tgtatcagat | 180 |
| cgcttttgat aatggctatt ccacgacttc taaaatccct gataccgcgc gaaactttga | 240 |
| aaatggcaat tatagtaaaa acagtgaaca aaaccacgca tggcaccca gcaattattc | 300 |
| tcgcaagttt ttagggcttg taaccttgca agaagccttg agccattcgt taaatctagc | 360 |
| cacgatcaat ttaagcgatc agcttggctt tgaaaaaatt tatcaatctt taagcgatat | 420 |
| ggggtttaaa aacctcccta aggacttgtc tattgtgtta gggagctttg ctatctcacc | 480 |
| cattgatgca gctgaaaagt | 500 |

```
<210> SEQ ID NO 51
<211> LENGTH: 600
<212> TYPE: DNA
<213> ORGANISM: Helicobacter pylori

<400> SEQUENCE: 51
```

| | |
|---|---:|
| atgaagatat tatcaccacc gttaaatacc tcatgaagat caaaaacaat caaggcaaga | 60 |
| ttgatgacag ggaccacttg gcaatcgta ggattagggc ggtaggggaa ttgttggcca | 120 |
| atgaattgca ttcaggttta gtgaaaatgc aaaagaccat taaagacaag ctcactacca | 180 |
| tgagcggggc ttttgattcg ctcatgcccc atgacttggt caattctaaa atgatcacaa | 240 |
| gcaccatcat ggaatttttc atgggcggtc agctctcgca atttatggat caaacgaatc | 300 |
| ccttgagtga ggttacgcac aagcgccgcc tttcagcgct cggcgaaggg gggttggtga | 360 |
| aagacagagt ggggtttgaa gccagggatg tgcaccccac gcattatggc cgaatttgtc | 420 |
| ccattgagac cccagaaggt caaaatatcg gtctgatcaa cacccttcc actttcacaa | 480 |
| gagtgaatga tttaggcttt attgaagccc cttataaaaa ggttgtggat ggcaaggtcg | 540 |
| tgggtgagac gatttatttg accgctattc aagaagacag ccacatcatc gctcccgcaa | 600 |

```
<210> SEQ ID NO 52
<211> LENGTH: 1032
<212> TYPE: DNA
<213> ORGANISM: Helicobacter pylori

<400> SEQUENCE: 52
```

| | |
|---|---:|
| atttgagcat gggcagatt ttaagcttat ttatggtaat tgtttcgtta gggattttat | 60 |
| tgtatgctac aaaaaattct aaaaaaataa aggaaaatca atgaaatttt tggatcaaga | 120 |
| aaaaagaaga caattattaa acgagcgcca ttcttgcaag atgtttgata gccattatga | 180 |

```
gttttctagc acagaattag aagaaatcgc tgaaatcgcc aggctatcgc caagctctta    240
caacacgcag ccatggcatt ttgtgatggt tactgataag gatttaaaaa aacaaattgc    300
agcgcacagc tatttcaatg aagagatgat taaaagcgct tcagcgttaa tggtggtatg    360
ctctttaaga cccagcgagt tgttaccaca cggccactac atgcaaaatc tctatccgga    420
gtcttataaa gttagagtga tcccctcttt tgctcaaatg cttggcgtga gattcaacca    480
cagcatgcaa agattagaaa gctatatttt agagcaatgc tatatcgctg tggggcaaat    540
ttgcatgggc gtgagcttaa tgggattgga tagttgcatt attggaggct ttgatccttt    600
aaaggtgggc gaagttttag aagagcgtat caataagcct aaaatcgcat gcttgatcgc    660
tttgggcaaa gggtggcaga agcgagtcaa aaatcaagaa atcaaaagt tgatgcgatt    720 acttggttgt gattaaacaa aatcaaaaac ttttaacta taatcaaacc taaattaaag    780
ttcaaggagt ggcattttgt ttaaaagaat ggttttaatc gctcttttag gggtgttttc    840
aagcgtttca ttaagcgcta agagtctttt aagagatgat gggattttag tctctgattt    900
aaagggcatg aaatcagaac tatctgatgc tcctgcttgg gtttttgaag acgctaaagc    960 ccccctacgaa gaaatgggcg tggcgtatat ccctgttaat aataaatatt tagggattga   1020
gcaagcgacc tt                                                        1032

<210> SEQ ID NO 53
<211> LENGTH: 143
<212> TYPE: DNA
<213> ORGANISM: Artificial
<220> FEATURE:
<223> OTHER INFORMATION: HPr01-23s rRNA_Clarithromycin_1

<400> SEQUENCE: 53
gggagctgtc tcaaccagag attcagtgaa attgtagtgg aggtgaaaat tcctcctacc     60
cgcggcaaga cggaaagacc ccgtggacct ttactacaac ttagcactgc taatgggaat    120
atcatgcgca ggataggtgg gag                                            143

<210> SEQ ID NO 54
<211> LENGTH: 112
<212> TYPE: DNA
<213> ORGANISM: Artificial
<220> FEATURE:
<223> OTHER INFORMATION: L-23S   CLARI-170R-F1_F03

<400> SEQUENCE: 54
ttgtagtgga ggtgaaaatt cctcctaccc gcggcaagac ggagagaccc cgtggacctt     60
tactacaact tagcactgct aatgggaata tcatgcgcag gataggtggg ag            112

<210> SEQ ID NO 55
<211> LENGTH: 112
<212> TYPE: DNA
<213> ORGANISM: Artificial
<220> FEATURE:
<223> OTHER INFORMATION: L-23S CLARI-194F_E03

<400> SEQUENCE: 55
ttgtagtgga ggtgaaaatt cctcctaccc gcggcaagac ggagagaccc cgtggacctt     60
tactacaact tagcactgct aatgggaata tcatgcgcag gataggtggg ag            112

<210> SEQ ID NO 56
<211> LENGTH: 112
<212> TYPE: DNA
```

```
<213> ORGANISM: Artificial
<220> FEATURE:
<223> OTHER INFORMATION: K-23S CLARI-170R-F1_D03

<400> SEQUENCE: 56
ttgtagtgga ggtgaaaatt cctcctaccc gcggcaagac ggaaagaccc cgtggacctt    60
tactacaact tagcactgct aatgggaata tcatgcgcag gataggtggg ag           112

<210> SEQ ID NO 57
<211> LENGTH: 112
<212> TYPE: DNA
<213> ORGANISM: Artificial
<220> FEATURE:
<223> OTHER INFORMATION: K-23S   CLARI-194F_C03

<400> SEQUENCE: 57
ttgtagtgga ggtgaaaatt cctcctaccc gcggcaagac ggaaagaccc cgtggacctt    60
tactacaact tagcactgct aatgggaata tcatgcgcag gataggtggg ag           112

<210> SEQ ID NO 58
<211> LENGTH: 142
<212> TYPE: DNA
<213> ORGANISM: Artificial
<220> FEATURE:
<223> OTHER INFORMATION: 5 fragment bases at  consensusposition 218

<400> SEQUENCE: 58
ggagctgtct caaccagaga ttcagtgaaa ttgtagtgga ggtgaaaatt cctcctaccc    60
gcggcaagac ggaaagaccc cgtggacctt tactacaact tagcactgct aatgggaata   120
tcatgcgcag gataggtggg ag                                            142

<210> SEQ ID NO 59
<211> LENGTH: 48
<212> TYPE: PRT
<213> ORGANISM: Artificial
<220> FEATURE:
<223> OTHER INFORMATION: 5 fragment bases at  consensusposition 218

<400> SEQUENCE: 59

Gly Ser Cys Leu Asn Gln Arg Phe Ser Glu Ile Val Val Glu Val Lys
1               5                   10                  15

Ile Pro Pro Thr Arg Gly Lys Thr Glu Arg Pro Arg Gly Pro Leu Leu
            20                  25                  30

Gln Leu Ser Thr Ala Asn Gly Asn Ile Met Arg Arg Ile Gly Gly Arg
        35                  40                  45
```